(12) United States Patent
Sison

(10) Patent No.: US 8,606,365 B2
(45) Date of Patent: Dec. 10, 2013

(54) IMPLANTABLE MEDICAL DEVICES, AND METHODS OF USE THEREWITH, THAT DETECT EXPOSURE TO MAGNETIC FIELDS FROM MRI SYSTEMS

(75) Inventor: Shiloh Sison, Alameda, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 13/442,692

(22) Filed: Apr. 9, 2012

(65) Prior Publication Data

US 2013/0268012 A1  Oct. 10, 2013

(51) Int. Cl.
*A61N 1/378* (2006.01)

(52) U.S. Cl.
USPC ............................................ 607/63; 607/2

(58) Field of Classification Search
USPC .................... 607/2, 115–116, 119, 18–19, 36; 600/300–301
See application file for complete search history.

(56) References Cited

U.S. PATENT DOCUMENTS

| 8,467,882 | B2* | 6/2013 | Ellingson et al. | 607/63 |
| 2009/0131996 | A1* | 5/2009 | Li | 607/4 |
| 2010/0106227 | A1* | 4/2010 | Min et al. | 607/63 |
| 2011/0152972 | A1* | 6/2011 | Doerr et al. | 607/62 |

\* cited by examiner

*Primary Examiner* — Carl H Layno
*Assistant Examiner* — Paula J Stice
(74) *Attorney, Agent, or Firm* — Steven M Mitchell

(57) ABSTRACT

Embodiments of the present invention generally pertain to implantable medical devices, and methods for use therewith, that detect exposure to magnetic fields produced by magnetic resonance imaging (MRI) systems. In accordance with specific embodiments, a sensor output is produced using an implantable sensor that is configured to detect acceleration, sound and/or vibration, but is not configured to detect a magnetic field. Such a sensor can be an accelerometer sensor, a strain gauge sensor or a microphone sensor, but is not limited thereto. In dependence on the produced sensor output, there is a determination whether of whether the IMD is being exposed to a time-varying gradient magnetic field from an MRI system. In accordance with certain embodiments, when there is a determination that the IMD is being exposed to a time-varying gradient magnetic field from an MRI system, then a mode switch to an MRI safe mode is performed.

24 Claims, 6 Drawing Sheets

IMPLANTABLE MEDICAL DEVICES, AND METHODS OF USE THEREWITH, THAT DETECT EXPOSURE TO MAGNETIC FIELDS FROM MRI SYSTEMS

FIELD OF THE INVENTION

Embodiments of the present invention generally pertain to implantable medical devices, and methods for use therewith, that detect exposure to magnetic fields produced by magnetic resonance imaging (MRI) systems.

BACKGROUND OF THE INVENTION

Implantable medical devices (IMDs) are implanted in patients to monitor, among other things, electrical cardiac activity, and to deliver appropriate cardiac electrical therapy, as required. IMDs include pacemakers, cardioverters, defibrillators, implantable cardioverter defibrillators (ICD), and the like. The electrical therapy produced by an IMD may include pacing pulses, cardioverting pulses, and/or defibrillator pulses to reverse arrhythmias (e.g., tachycardias and bradycardias) or to stimulate the contraction of cardiac tissue (e.g., cardiac pacing) to return the heart to its normal sinus rhythm. IMDs can also be used to perform cardiac resynchronization therapy (CRT).

When IMDs are exposed to external magnetic fields, such as those produced by magnetic resonance imaging (MRI) systems, the magnetic fields may interfere with operation of the IMDs. For example, such external magnetic fields may generate magnetic forces on an IMD and the leads and electrodes attached to the IMD. These forces may induce electric charges or potentials on the leads and electrodes, which can cause over- or under-sensing of cardiac signals. For example, the charges may cause the electrodes and leads to convey signals to an IMD that are not cardiac signals, but are treated by the IMO as cardiac signals. This may cause the IMD to falsely detect tachycardias (which do not actually exist), potentially causing the IMD to delivery anti-tachycardia pacing (ATP) or defibrillation shock therapy (when not actually necessary). In another example, the charges induced by MRI systems may induce sufficient noise in cardiac signals such that cardiac signals that are representative of cardiac events go undetected by an IMD. This may cause the IMD to not detect a tachycardia (which actually exists), potentially causing the ND to not delivery appropriate anti-tachycardia pacing (ATP) or defibrillation shock therapy (when actually necessary). This may also cause the IMD to not deliver pacing therapy since it falsely believes there are intrinsic cardiac events ongoing.

An MRI system generally produces and utilizes three types of electromagnetic fields, which include a strong static magnetic field, a time-varying gradient magnetic field, and a radio frequency (RF) magnetic field, which can collectively be referred to as the magnetic field from an MRI system. The time-varying gradient field and the RF field may be referred to as different parts of the time-varying magnetic field. In other words, the time-varying gradient field and the RF field can collectively be referred to as the time-varying magnetic field. The static field produced by most MRI systems has a magnetic induction ranging from about 0.35 Tesla (T) to about 4 T, but can be potentially higher (e.g., 7 T and 9 T MRI systems are sometimes used in research). More specifically, MRI systems may generate external static magnetic fields having different strengths, such as 0.35 T, 0.5 T, 0.7 T, 1.0 T, 1.2 T, 1.5 T, 3 T, 4 T etc. The RF field includes RF pulses. The frequency of the RF field is related to the magnitude of the static magnetic field, with the frequency of the RF field being approximately 42.58e6* static field strength. For example, where the static magnetic field strength is 1.5 T, the RF is at 42.58e6*1.5~64 MHz; and where the static magnetic field is 3 T, the RF is at 42.58e6*3~128 MHz. The time-varying gradient magnetic field, which is used for spatial encoding, typically has a frequency in the KHz range, but for many MRI sequences can have relatively high power in the sub-KHz range.

In order to safely operate while exposed to magnetic fields produced by MRI systems, IMDs may switch modes to an "MRI safe mode". Some IMDs require that a clinician send a telemetry command to the IMDs, via a special external programmer, in order to put the IMDs in an MRI safe mode. However, the need for this special external programmer and for clinician training on using the external programmer are time consuming, costly and cumbersome. Further, this protocol may not be properly followed, e.g., in emergency situations, when the technician operating the MRI system is not aware that the patient has an IMD, and/or when an appropriate external programmer is unavailable.

An IMD's failure to switch from its normal operational mode into an MRI safe mode, when it should have, may cause the IMD to inhibit necessary pacing, or delivery unnecessarily high voltage therapy or anti-tachycardia pacing, which may induce an arrhythmia. Further, failure of an IMD to switch out of an MRI safe mode and back to its normal operational mode, when it should have, may cause pacing that leads to non-optimal therapy, loss of rate-response, pacemaker syndrome, and/or other problems.

In order to sense and detect external magnetic fields, some IMDs include giant magnetoresistance (GMR) sensors. Known GMR sensors are typically configured to detect magnetic fields of relatively small magnitudes produced by a handheld magnet. The GMR sensor operates by detecting a change in an electrical resistance characteristic of the sensor when the sensor transitions from not being exposed to a magnetic field to being exposed to a magnetic field. In response, the IMD may switch to a "magnet mode" of operation. During the magnet mode of operation, the IMD may, e.g., pace the ventricle(s) at a predetermined fixed rate without sensing cardiac signals or responding to any detected cardiac events. Alternatively, or additionally, when in the magnet mode the IMD may record of an intracardiac electrogram (IEGM) for subsequent evaluation. The IMD's operation when in "magnet mode" may depend on the brand of IMD, the type of IMD, the level of battery charge in the device, and more generally, how the magnet mode is defined for the specific IMD and/or patient. In some IMDs, the magnet mode may shut off the device. As the terms are used herein, a magnet mode and an MRI safe mode refer to different modes of operation for an IMD, although there may be some overlap as to how the IMD operates in its magnet mode and its MRI safe mode (e.g., in both modes, the IMD may pace without sensing cardiac signals). It is even possible that a physician may program the magnet mode and the MRI safe mode to be the same or similar for a specific patient.

Conventional GMR sensors used in IMDs are typically formed from materials that may become saturated when exposed to relatively small magnetic fields, and most likely will become saturated when exposed to the relatively strong magnetic fields produced by MRI systems. For example, some known GMR sensors become saturated when exposed to magnetic fields of as low as 15 Gauss (G), where $1\ G=1\times 10^{-4}\ T$. Once the GMR sensor is saturated, further increases in the external magnetic field are not detected by the GMR sensor. Accordingly, conventional GMR sensors may be unable to reliably sense relatively strong external magnetic fields. As a result, the GMR sensors may be incapable of detecting the presence of external magnetic fields generated by MRI systems. Also, GMR sensors may be unable to differentiate between different strengths of magnetic fields. For example, GMR sensors may be incapable of differentiating between relatively small external magnetic fields (e.g., produced by a relatively small handheld magnet) intended to switch an IMD into its magnetic mode and/or in which the IMD may continue to safely operate, and relatively strong external magnetic fields generated by an MRI system, in which the IMD may be unable to safely operate unless switched into an MRI safe mode. For another example, where a patient's legs (or head) are within the high static magnetic field of an MRI system, while the patient's torso (in which an IMD with a GMR sensor is implanted) is outside the high static magnetic field of the MRI system, the magnitude of the magnetic field detected by the GMR sensor may be similar to that of a handheld magnet. This may cause the IMD to switch into its magnet mode, when it actually should have switched into an MRI safe mode. Similar problems to those discussed above with regard to GMR sensors can also arise where an IMD includes a Hall effect sensor or a reed switch for the purpose of detecting a handheld magnet. For example, where an IMD includes a Hall effect sensor for the purpose of detecting a handheld magnet (for use in switching the IMD to a magnet mode), the Hall effect sensor may not be able to distinguish between magnetic fields produced by a handheld magnet and an MRI system (e.g., where a patient's legs or head are within the high static magnetic field of an MRI system, while the patient's torso is outside the high static magnetic field of the MRI system).

Therefore, a need still exists for IMDs, and methods for use therewith, that can accurately detect the exposure of the IMDs to magnetic fields generated by MRI systems.

SUMMARY OF THE INVENTION

Embodiments of the present invention generally pertain to implantable medical devices, and methods for use therewith, that detect exposure to magnetic fields produced by magnetic resonance imaging (MRI) systems. In accordance with specific embodiments, a sensor output is produced using an implantable sensor that is configured to detect acceleration, sound and/or vibration, but is not configured to detect a magnetic field. Such a sensor can be an accelerometer sensor, a strain gauge sensor or a microphone sensor, but is not limited thereto. In dependence on the produced sensor output, there is a determination of whether the IMD is being exposed to a time-varying gradient magnetic field from an MRI system.

In accordance with specific embodiments, performance of the aforementioned steps are triggered when an implantable GMR sensor, reed switch or Hall effect sensor of the IMD detects a magnetic field.

In certain embodiments, the output of the implantable sensor configured to detect acceleration, sound and/or vibration (but not a magnetic field) can be used to confirm or reject the determination, using an implantable static magnetic field detector sensor (e.g., a Hall effect sensor), that the IMD is being exposed to a magnetic field from an MRI system. In certain embodiments, the output of the implantable sensor configured to detect acceleration, sound and/or vibration (but not a magnetic field) can be used to distinguish between the IMD being exposed to a magnetic field from a handheld magnet, and the IMD is being exposed to a magnetic field from an MRI system.

In the above described embodiments, the accelerometer (or other sensor configured to detect acceleration, sound and/or vibration) is not actually detecting the magnetic field from an MRI system, but rather, detects secondary acoustic and/or vibratory effects of an MRI system. That is, while an intended purpose of an MRI system is to generate time-varying gradient magnetic fields, unintended but inevitable results of generating the time-varying gradient magnetic fields are relatively loud noises and vibrations Embodiments of the present invention take advantage of such unintended but inevitable secondary acoustic and/or vibratory effects of an MRI system.

In accordance with certain embodiments, when there is a determination that the IMD is being exposed to a time-varying gradient magnetic field from an MRI system, then a mode switch to an MRI safe mode is performed. Additionally, when there is a determination that the IMD is no longer being exposed to a time-varying gradient magnetic field from an MRI system, then a mode switch to a normal operational mode can be performed.

In specific embodiments, the frequency content of the sensor output (produced using the implantable sensor configured to detect acceleration, sound and/or vibration, but not a magnetic field) is estimated or otherwise determined. In such embodiments, the determination (of whether the IMD is being exposed to a time-varying gradient magnetic field from an MRI system) is based on the estimated or otherwise determined frequency content of the sensor output. The frequency content of the sensor output can be determined, e.g., by performing a fast Fourier transform (FFT) and/or a wavelet transformation of the sensor output, or by determining the power spectral density (PSD) of the sensor output. Alternatively, or additionally, the sensor output can be analyzed in the time domain, e.g., by counting a number of zero crossings, peaks or other signal features within a window of one or more signals output by the implantable sensor. In specific embodiments, the morphology of one or more signals output by the implantable sensor (or the frequency and/or time based content thereof) is/are compared to one or more template(s) corresponding to one or more representative sets of time-varying gradient magnetic field sequences produced by MRI systems. In such embodiments, the determination (of whether the IMD is being exposed to a time-varying gradient magnetic field from an MRI system) is based the results of such comparison(s).

This summary is not intended to be a complete description of the invention. Other features and advantages of the invention will appear from the following description in which the preferred embodiments have been set forth in detail, in conjunction with the accompanying drawings and claims.

DETAILED DESCRIPTION OF PREFERRED EMBODIMENTS

Figure 1:
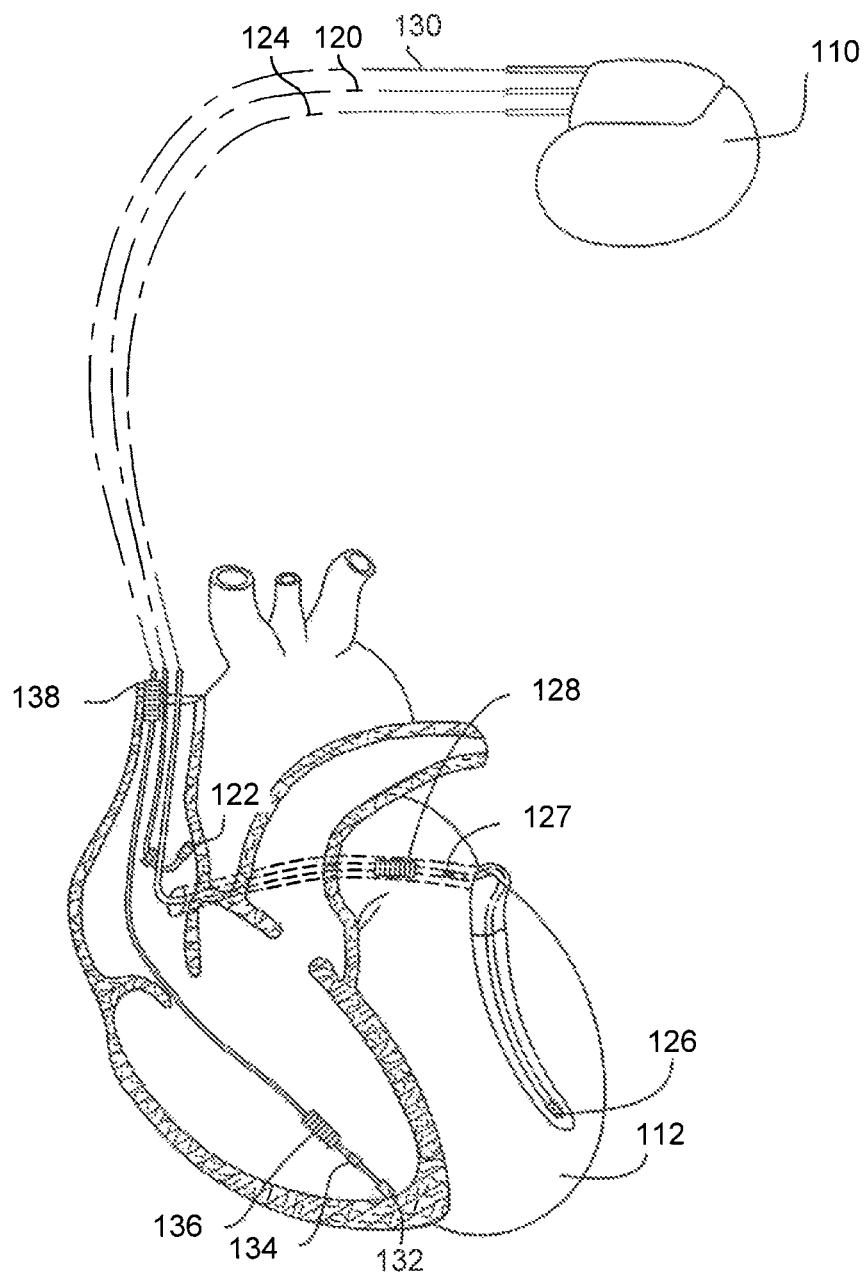
FIG. 1 is a simplified, partly cutaway view illustrating an implantable stimulation device for delivering stimulation and/or shock therapy.

The following description is of the best modes presently contemplated for practicing various embodiments of the present invention. The description is not to be taken in a limiting sense but is made merely for the purpose of describing the general principles of the invention. The scope of the invention should be ascertained with reference to the claims. In the description of the invention that follows, like numerals or reference designators will be used to refer to like parts or elements throughout. In addition, the first digit of a reference number identifies the drawing in which the reference number first appears.

The disclosed embodiments of the present invention generally pertain to IMDs, and methods for use therewith, that detect exposure to time-varying gradient magnetic fields produced by MRI systems. Accordingly, an exemplary IMD in which embodiments of the present invention are useful is first described with reference to FIGS. 1 and 2. However, it should be noted that embodiments of the present invention are not limited to use with the exemplary IMD described below.

Exemplary IMD

Referring to FIG. 1, an exemplary IMD 110 (also referred to as a pacing device, a pacing apparatus, a stimulation device, an implantable device or simply a device) is in electrical communication with a patient's heart 112 by way of three leads, 120, 124 and 130, suitable for delivering multi-chamber stimulation. While not necessary to perform embodiments of the present invention, the exemplary IMD 110 is also capable of delivering shock therapy.

To sense atrial cardiac signals and to provide right atrial chamber stimulation therapy, the IMD 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the IMD 110 is coupled to a "coronary sinus" lead 124 designed for placement in the "coronary sinus region" via the coronary sinus for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive left atrial and ventricular cardiac signals and to deliver left atrial and ventricular pacing therapy using at least a left ventricular tip electrode 126, left atrial pacing therapy using at least a left atrial ring electrode 127, and shocking therapy using at least a left atrial coil electrode 128. The present invention may of course be practiced with a coronary sinus lead that does not include left atrial sensing, pacing or shocking electrodes.

The IMD 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricle and the SVC coil electrode 138 will be positioned in the superior vena cava. Accordingly, the right ventricular lead 130 is capable of receiving cardiac signals and delivering stimulation in the form of pacing and shock therapy to the right ventricle. It will be understood by those skilled in the art that other lead and electrode configurations such as epicardial leads and electrodes may be used in practicing the invention. For example, only a single lead, or only two leads, may be connected to the IMD. It should also be understood that the IMD can alternatively be a leadless device, such as an implantable monitor and/or a leadless pacer.

Figure 2:
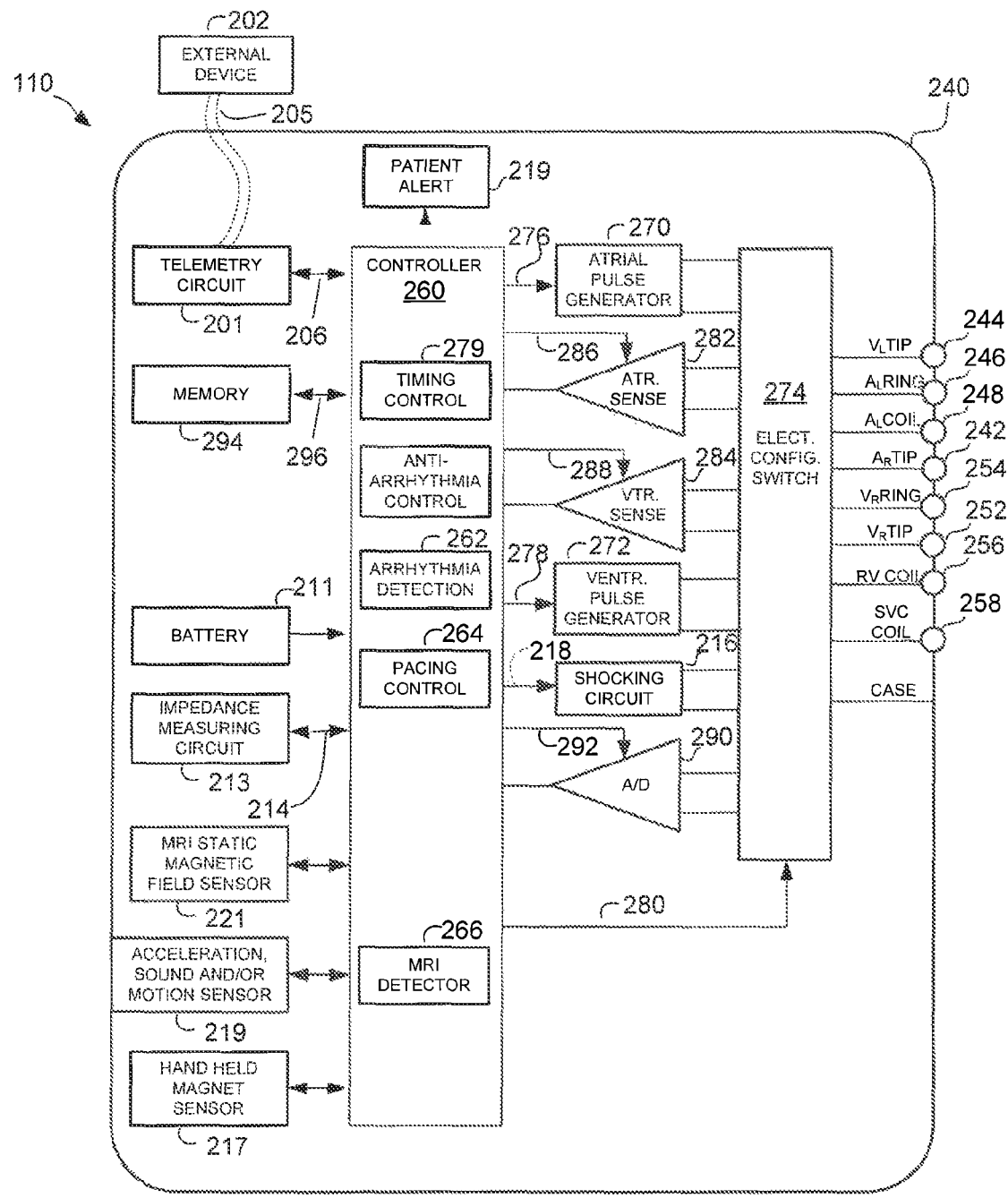
FIG. 2 is a functional block diagram of the implantable stimulation device of FIG. 1, illustrating the basic elements that provide pacing stimulation, cardioversion, and defibrillation in chambers of the heart.

As illustrated in FIG. 2, a simplified block diagram is shown of the multi-chamber implantable device 110, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 240 for the IMD 110, shown schematically in FIG. 2, is often referred to as the "can", "case" or "case electrode" and may be programmably selected to act as the return electrode for all "unipolar" modes. The housing 240 may further be used as a return electrode alone or in combination with one or more of the coil electrodes, 128, 136 and 138, for shocking purposes. The housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 122.

To achieve left atrial and ventricular sensing, pacing and shocking, the connector includes at least a left ventricular tip terminal ($V_L$ TIP) 244, a left atrial ring terminal ($A_L$ PING) 246, and a left atrial shocking terminal ($A_L$ COIL) 148, which are adapted for connection to the left ventricular ring electrode 126, the left atrial tip electrode 127, and the left atrial coil electrode 128, respectively.

To support right ventricle sensing, pacing and shocking, the connector further includes a right ventricular tip terminal ($V_R$ TIP) 252, a right ventricular ring terminal ($V_R$ RING) 254, a right ventricular shocking terminal ($R_V$ COIL) 256, and an SVC shocking terminal (SVC COIL) 258, which are adapted for connection to the right ventricular tip electrode 132, right ventricular ring electrode 134, the RV coil electrode 136, and the SVC coil electrode 138, respectively.

At the core of the IMD 110 is a programmable microcontroller 260 which controls the various types and modes of stimulation therapy. As is well known in the art, the microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art. In specific embodiments of the present invention, the microcontroller 260 performs some or all of the steps associated with arrhythmia detection.

Representative types of control circuitry that may be used with the invention include the microprocessor-based control system of U.S. Pat. No. 4,940,052 (Mann et. al.) and the state-machines of U.S. Pat. No. 4,712,555 (Sholder) and U.S. Pat. No. 4,944,298 (Sholder). For a more detailed description of the various timing intervals used within the pacing device and their inter-relationship, see U.S. Pat. No. 4,788,980 (Mann et. al.). The '052, '555, '298 and '980 patents are incorporated herein by reference.

An atrial pulse generator 270 and a ventricular pulse generator 272 generate pacing stimulation pulses for delivery by the right atrial lead 120, the right ventricular lead 130, and/or the coronary sinus lead 124 via an electrode configuration switch 274. It is understood that in order to provide stimulation therapy in each of the four chambers of the heart, the atrial and ventricular pulse generators, 270 and 272, may include dedicated, independent pulse generators, multiplexed pulse generators, or shared pulse generators. The pulse generators, 270 and 272, are controlled by the microcontroller 260 via appropriate control signals, 276 and 278, respectively, to trigger or inhibit the stimulation pulses.

The microcontroller 260 further includes timing control circuitry 279 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, etc.) by selectively closing the appropriate combination of switches (not shown) as is known in the art.

Atrial sensing circuits 282 and ventricular sensing circuits 284 may also be selectively coupled to the right atrial lead 120, coronary sinus lead 124, and the right ventricular lead 130, through the switch 274 for detecting the presence of cardiac activity in each of the four chambers of the heart. Accordingly, the atrial (ATR. SENSE) and ventricular (VTR. SENSE) sensing circuits, 282 and 284, may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit, 282 and 284, preferably employs one or more low power, precision amplifiers with programmable gain and/or automatic gain control, bandpass filtering, and a threshold detection circuit, as known in the art, to selectively sense the cardiac signal of interest. The automatic gain control enables the IMD 110 to deal effectively with the difficult problem of sensing the low amplitude signal characteristics of atrial or ventricular fibrillation. Such sensing circuits, 282 and 284, can be used to determine cardiac performance values used in the present invention. Alternatively, an automatic sensitivity control circuit may be used to effectively deal with signals of varying amplitude.

The outputs of the atrial and ventricular sensing circuits, 282 and 284, are connected to the microcontroller 260 which, in turn, are able to trigger or inhibit the atrial and ventricular pulse generators, 270 and 272, respectively, in a demand fashion in response to the absence or presence of cardiac activity, in the appropriate chambers of the heart. The sensing circuits, 282 and 284, in turn, receive control signals over signal lines, 286 and 288, from the microcontroller 260 for purposes of measuring cardiac performance at appropriate times, and for controlling the gain, threshold, polarization charge removal circuitry (not shown), and timing of any blocking circuitry (not shown) coupled to the inputs of the sensing circuits, 282 and 286. The sensing circuits can be used, for example, to acquire IEGM signals.

For arrhythmia detection, the IMD 110 includes an arrhythmia detector 262 that utilizes the atrial and ventricular sensing circuits, 282 and 284, to sense cardiac signals to determine whether a rhythm is physiologic or pathologic. The timing intervals between sensed events (e.g., P-waves, R-waves, and depolarization signals associated with fibrillation) are then classified by the microcontroller 260 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to assist with determining the type of remedial therapy that is needed (e.g., bradycardia pacing, anti-tachycardia pacing, cardioversion shocks or defibrillation shocks, collectively referred to as "tiered therapy"). The arrhythmia detector 262 can be implemented within the microcontroller 260, as shown in FIG. 2. Thus, this detector 262 can be implemented by software, firmware, or combinations thereof. It is also possible that all, or portions, of the arrhythmia detector 262 can be implemented using hardware. Further, it is also possible that all, or portions, of the arrhythmia detector 262 can be implemented separate from the microcontroller 260.

The stimulation device 110 is also shown as including a pacing controller 264, which can adjust a pacing rate and/or pacing intervals. The pacing controller 264 can be implemented within the microcontroller 260, as shown in FIG. 2. Thus, the pacing controller 264 can be implemented by software, firmware, or combinations thereof. It is also possible that all, or portions, of the pacing controller 264 can be implemented using hardware.

Additionally, the IMD 110 is shown as including an MRI detector 266, which can detect when the IMD 110 is being exposed to a magnetic field from an MRI system. Additional details of the operation of the MRI detector 266, according to various embodiments of the present invention, are discussed below. The MRI detector 266 can be implemented within the microcontroller 260, as shown in FIG. 2. Thus, the MRI detector 266 can be implemented by software, firmware, or combinations thereof. It is also possible that all, or portions, of the MRI detector 266 can be implemented using hardware.

The IMD 110 is also shown as including a sensor 219 that is configured to detect acceleration, sound and/or vibration, but is not configured to detect a magnetic field. As will be described in additional detail below, despite not being configured to detect a magnetic field, in accordance with embodiments of the present invention, the MRI detector 266 can use the output of the sensor 219 to detect when the IMD 110 is being exposed to a time-varying gradient magnetic field from an MRI system.

In certain embodiments, the sensor 219 can be an accelerometer, such as, but not limited to, a 1-dimensional accelerometer, a 2-dimensional accelerometer or a 3-dimensional accelerometer. An accelerometer is often included in an implantable device, such as the IMD 110, for the purpose of monitoring patient position and/or patient activity. Embodiments of the present invention, as will be discussed in further detail below, can alternatively or additionally use an existing accelerometer to determine whether the IMD 110 is being exposed to a time-varying gradient magnetic field from an MRI system. For example, where an accelerometer is already included in the IMD 110 for the purpose of detecting posture and/or patient activity (e.g., for use in rate responsive pacing), the firmware of the IMD 110 can be initially programmed or updated to also rely on the accelerometer for determining whether the IMD 110 is being exposed to a time-varying gradient magnetic field from an MRI system. In other words, the sensor output of an accelerometer can be used for both controlling rate responsive pacing as well for determining whether the IMD 110 is being exposed to a time-varying gradient magnetic field from an MRI system. It is also possible that one accelerometer be used for rate responsive pacing, and a second (potentially more sensitive) accelerometer be used for determining whether the IMD 110 is being exposed to a time-varying gradient magnetic field from an MRI system. In the above mentioned embodiments, the accelerometer (or other type of sensor 219) is not actually detecting the magnetic field from an MRI system, but rather, detects secondary acoustic and/or vibratory effects of an MRI system. That is, while an intended purpose of an MRI systems is to generate time-varying gradient magnetic fields, unintended but inevitable results of generating the time-varying gradient magnetic fields are relatively loud noises and vibrations. Embodiments of the present invention take advantage of such unintended but inevitable secondary acoustic and/or vibratory effects of an MRI system.

While a 1-dimensional accelerometer can be used, it is preferable to use a multi (two or more) axis accelerometer because they can be used to detect acceleration, sound and/or vibration along more than one axis, and thus, are more likely to detect acceleration, sound and/or vibration regardless of the relative positions of the sensor and the time-varying gradient magnetic field that the sensor is being used to detect.

Accelerometers typically include two or three sensors aligned along orthogonal axes. Exemplary multi-axis accelerometers (also referred to as multi-dimensional accelerometers) that can be used are described U.S. Pat. Nos. 6,658,292 (Kroll et al.) and 6,466,821 (Pianca et al.), each of which is incorporated herein by reference. For another example, a commercially available micro-electromechanical system (MEMS) accelerometer marketed as the ADXL345 by Analog Devices, Inc. (headquartered in Norwood, Mass.) is a three-axis accelerometer and includes polysilicon springs that provide a resistance against acceleration forces. The term MEMS has been defined generally as a system or device having micro-circuitry on a tiny silicon chip into which some mechanical device such as a mirror or a sensor has been manufactured. The aforementioned ADXL345 includes a micro-machined accelerometer co-packaged with a signal processing IC.

Another commercially available MEMS accelerometer is the ADXL327 by Analog Devices, Inc., which is a small, thin, low power, complete three axis accelerometer with signal conditioned voltage outputs. In the ADXL327, the mechanical sensor and signal conditioning IC are packaged together. A further commercially available MEMS accelerometer that can be used is the LIS3DH three-axis accelerometer by STMicroelectronics (headquartered in Geneva, Switzerland).

Additional and/or alternative types of accelerometers may also be used. For example, it is also within the scope of the present invention for the sensor 219 to be a beam-type of accelerometer, an example of which is described in U.S. Pat. No. 6,252,335 (Nilsson et al.), which is incorporated herein by reference.

In certain embodiment, the sensor 219 is implemented using one or more strain gauges. For example, a conventional type of strain gauge is formed of a thin film with a conductive wire or wires and associated terminals where tension causes an increase in resistance at the terminals and where compression decreases resistance at the terminals (e.g., a piezoresistive gauge). Vibrations and/or acoustics may cause such a film to cycle between tension and compression and hence produce an oscillating signal as resistance changes. The oscillating signal may be analyzed to determine the frequency of oscillation and/or the morphology of the signal. A strain gauge may be configured to sense strain along a particular direction. Multiple strain gauges may be included in the sensor 219 to sense strain along different directions.

It is also possible that the sensor 219 is implemented as a microphone, which can be use for sensing vibration and/or acoustics. A microphone sensor can include a diaphragm and associated electronics that can alter a signal as energy impacts the diaphragm. Piezoelectric microphones, for example, rely on the ability of a material to produce a voltage when subject to pressure and to convert vibrations into an electrical signal. For another example, MEMS microphones, available from Akustica, Inc. (headquartered in Pittsburgh, Pa.), include a pressure-sensitive diaphragm etched directly on a silicon chip.

Strain gauge and/or microphone type sensors 219 may be included in an implantable device, such as IMD 110, to detect heart sounds, e.g., for the purpose of assessing electromechanical delays of the heart, assisting with arrhythmia discrimination, and/or assessing homodynamic status. Embodiments of the present invention, can alternatively or additional use such strain gauge and/or microphone type sensors 219 to determine whether the IMD 110 is being exposed to a time-varying gradient magnetic field from an MRI system. In such embodiments, the strain gauge and/or microphone type sensors 219 is/are not actually detecting the magnetic field from an MRI system, but rather, detect secondary acoustic and/or vibratory effects of an MRI system.

The sensor 219 may be included within the case 240 of the implantable device 110. It is also possible that the sensor 219 is attached to, or integrally formed with, the case 240. For example, U.S. Pat. Nos. 6,477,406 (Turcott) and 6,527,729 (Turcott), which are incorporated herein by references, disclose examples of acoustic sensors included within the case and integrally formed with the case. Alternatively, the sensor 219 can be included in or be otherwise be attached to a lead (e.g., 120, 124 or 130), in which case the sensor 219 can communicate with the IMD 110 via the lead or through electrical signals conducted by body tissue and/or fluid. For example, an exemplary lead can include the sensor 219 (e.g., an accelerometer or other sensor) proximate to one end and a connector at the other end that allows for connection to an implantable device such as the IMD 110.

Signals produced and output by the sensor 219 may be analyzed with respect to frequency content, energy, duration, amplitude and/or other characteristics. Such signals may or may not be amplified and/or filtered prior to being analyzed. For example, filtering may be performed using lowpass, highpass and/or bandpass filters. The signals output by the sensor 219 can be analog signals, which can be analyzed in the analog domain, or can be converted to digital signals (by an analog-to-digital converter, e.g., 290) and analyzed in the digital domain. Alternatively, the signals output by the sensor 219 can already be in the digital domain. The signals output by the sensor 219 can be analyzed by the microcontroller 260 and/or other circuitry. In certain embodiments, the sensor 219 is packaged along with an integrated circuit (IC) that is designed to analyze the signals output by the sensor 219. In such embodiments, an output of the packaged sensor/IC can be an indication as to whether or not a time-varying gradient magnetic field from an MRI system is detected. In other embodiments, the sensor 219 can be packaged along with an IC that performs signal conditioning (e.g., amplification and/or filtering), performs analog-to-digital conversions, and stores digital data (indicative of the sensor output) in memory (e.g., RAM, which may or may not be within the same package). In such embodiments, the microcontroller 260 or other circuitry can read the digital data from the memory and analyze the digital data. Other variations are also possible, and within the scope of the present invention. Additional details of how to analyze signals output by the sensor 219 are discussed below.

The IMD 110 is also shown as including a handheld magnet sensor 217, which is used to detect when a relatively small static magnetic field produced by a handheld magnet is placed in the vicinity of the stimulation device 110 for the purpose of initiating a preprogrammed "magnet mode" of operation (which is distinct from an MRI safe mode) and/or a preprogrammed function (e.g., recording of an IEGM). For example, a patient may place a handheld magnet near their chest when the patient detects an abnormality in the function of either their heart or their implanted stimulation device. The sensor 217, in response to detecting the magnetic field, can trigger the recording of an IEGM for subsequent evaluation, and/or can trigger a mode switch to a magnet mode of operation that is specified by a physician or is specified by default. The sensor 217 can be, e.g., a GMR sensor. An exemplary GMR sensor is described in U.S. Pat. No. 6,101,417, which is incorporated herein by reference. For another example, commercially available GMR sensors are manufactured and sold by NVE Corporation (headquartered in Eden Prairie, Minn.). Exemplary GMR sensors produced by NVE Corporation include the BA010-01, BA020 and BD027-14E sensors. It is also possible that a reed switch or a Hall effect sensor can be used as the handheld magnet sensor 217, as is well known in the art. The GMR sensor, reed switch or Hall effect sensor may also be used by a clinician to perform various test functions of the IMD 110 and/or to signal the microcontroller 260 that the external programmer 202 is in place to receive or transmit data to the microcontroller 260 through the telemetry circuits 201.

The IMD 110 optionally includes an MRI static magnetic field detector sensor 221 that is capable of detecting the relatively large static magnetic fields produced by MRI systems. As will be described in additional detail below, when the device 110 includes such a sensor 221, the sensor 219 (which is configured to detect acceleration, sound and/or vibration) can be used to confirm or reject a determination, using the MRI static magnetic field detector sensor 221, that the device 110 is being exposed to a magnetic field from an MRI system. The MRI static magnetic field detector sensor 221 can be, e.g., a Hall effect sensor, but is not limited thereto. It is also possible that the sensors 217 and 221 can be implemented using a single sensor (e.g., a Hall effect sensor) and two thresholds, e.g., a low threshold and a high threshold. For example, if the high threshold is exceeded it can be determined that a relatively high static magnetic field produced by an MRI system is detected; and if only the low threshold (but not the high threshold) is exceeded it can be determined that a relatively low magnetic field produced by a handheld magnet is detected.

Still referring to FIG. 2, cardiac signals and/or other signals can be applied to the inputs of an analog-to-digital (ND) data acquisition system 290. The data acquisition system 290 is configured to acquire intracardiac electrogram signals, convert the raw analog data into a digital signal, and store the digital signals for later processing and/or telemetric transmission to an external device 202. The data acquisition system 290 is coupled to the right atrial lead 120, the coronary sinus lead 124, and the right ventricular lead 130 through the switch 274 to sample cardiac signals across any pair of desired electrodes.

The data acquisition system 290 can be coupled to the microcontroller 260, or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred. The data acquisition system 290 may also be used to acquire signals produced by the sensors 217, 219 and/or 221, and may convert analog signals produced by such sensor to digital signals. It is also possible that the sensors 217, 219 and/or 221 output digital signals.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et. al.); and U.S. Pat. No. 5,350,410 (Mann et. al.), which patents are hereby incorporated herein by reference. The type of capture detection system used is not critical to the present invention.

The microcontroller 260 is further coupled to the memory 294 by a suitable data/address bus 296, wherein the programmable operating parameters used by the microcontroller 260 are stored and modified, as required, in order to customize the operation of the IMD 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 112 within each respective tier of therapy. The memory 294 can also be used to store data relating to time-varying magnetic field sequences used by known MRI systems, morphological templates, threshold values, and other information that can be utilized in embodiments of the present invention described herein. For a specific example, the memory 294 can be used to store data (such as templates) specifying the frequency and/or time based content corresponding to one or more representative sets of time-varying gradient magnetic field sequences produced by MRI systems.

The operating parameters of the IMD 110 may be noninvasively programmed into the memory 294 through a telemetry circuit 201 in telemetric communication with an external device 202, such as a programmer, transtelephonic transceiver, or a diagnostic system analyzer. The telemetry circuit 201 can be activated by the microcontroller 260 by a control signal 206. The telemetry circuit 201 advantageously allows intracardiac electrograms and status information relating to the operation of the device 110 (as contained in the microcontroller 260 or memory 294) to be sent to the external device 202 through an established communication link 204. The telemetry circuit 201 can also be used to trigger alarms or alerts of the external device 202, or to instruct the external device 202 to notify a caregiver regarding detection of various episodes, occurrences and changes in conditions that are detected using embodiments of the present invention.

For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The IMD 110 additionally includes a battery 211 which provides operating power to all of the circuits shown in FIG. 2. If the implantable device 110 also employs shocking therapy, the battery 211 should be capable of operating at low current drains for long periods of time, and then be capable of providing high-current pulses (for capacitor charging) when the patient requires a shock pulse. The battery 211 should also have a predictable discharge characteristic so that elective replacement time can be detected.

As further shown in FIG. 2, the IMD 110 is also shown as having an impedance measuring circuit 213 which is enabled by the microcontroller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 213 is advantageously coupled to the switch 274 so that any desired electrode may be used. The impedance measuring circuit 213 is not critical to the present invention and is shown only for completeness.

In the case where the IMD 110 is also intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 260 further controls a shocking circuit 216 by way of a control signal 218. The shocking circuit 216 generates shocking pulses of low (up to 0.5 Joules), moderate (0.5-10 Joules), or high energy (11 to 40 Joules), as controlled by the microcontroller 260. Such shocking pulses are applied to the patient's heart 112 through at least two shocking electrodes, and as shown in this embodiment, selected from the left atrial coil electrode 228, the RV coil electrode 236, and/or the SVC coil electrode 238. As noted above, the housing 240 may act as an active electrode in combination with the RV electrode 236, or as part of a split electrical vector using the SVC coil electrode 238 or the left atrial coil electrode 228 (i.e., using the RV electrode as a common electrode).

The above described IMD 110 was described as an exemplary pacing device. One or ordinary skill in the art would understand that embodiments of the present invention can be used with alternative types of implantable devices. Accordingly, embodiments of the present invention should not be limited to use only with the above described device.

Preferred Embodiments of the Present Invention

As mentioned above, in order to avoid under- or over-sensing the cardiac signals when the IMD 110 is in the presence of relatively large external magnetic fields produced by an MRI system, the IMD 110 may switch modes of operation from a normal mode to an MRI safe mode when the IMD 110 enters or is otherwise exposed to the magnetic field. While in the MRI safe mode, the IMD 110 may change the algorithms, software, and/or logical steps by which cardiac signals are monitored, and/or by which pacing and/or other cardiac therapy is delivered. For example, the IMD 110 may change which algorithms are used to identify an arrhythmia. Alternatively, the IMD 110 may cease measuring or sensing cardiac signals. Once the IMD 110 leaves or is otherwise not exposed to the strong magnetic field from an MRI system, the IMD 110 may switch back to its normal mode of operation, which is also referred to as the normal operational mode. In the normal operational mode, the IMD 110 may resume monitoring cardiac signals as the IMD 110 did before the IMD 110 was exposed to a strong magnetic field from an MRI system. Exemplary normal operational modes and MRI safe modes are discussed below.

Figure 3A:
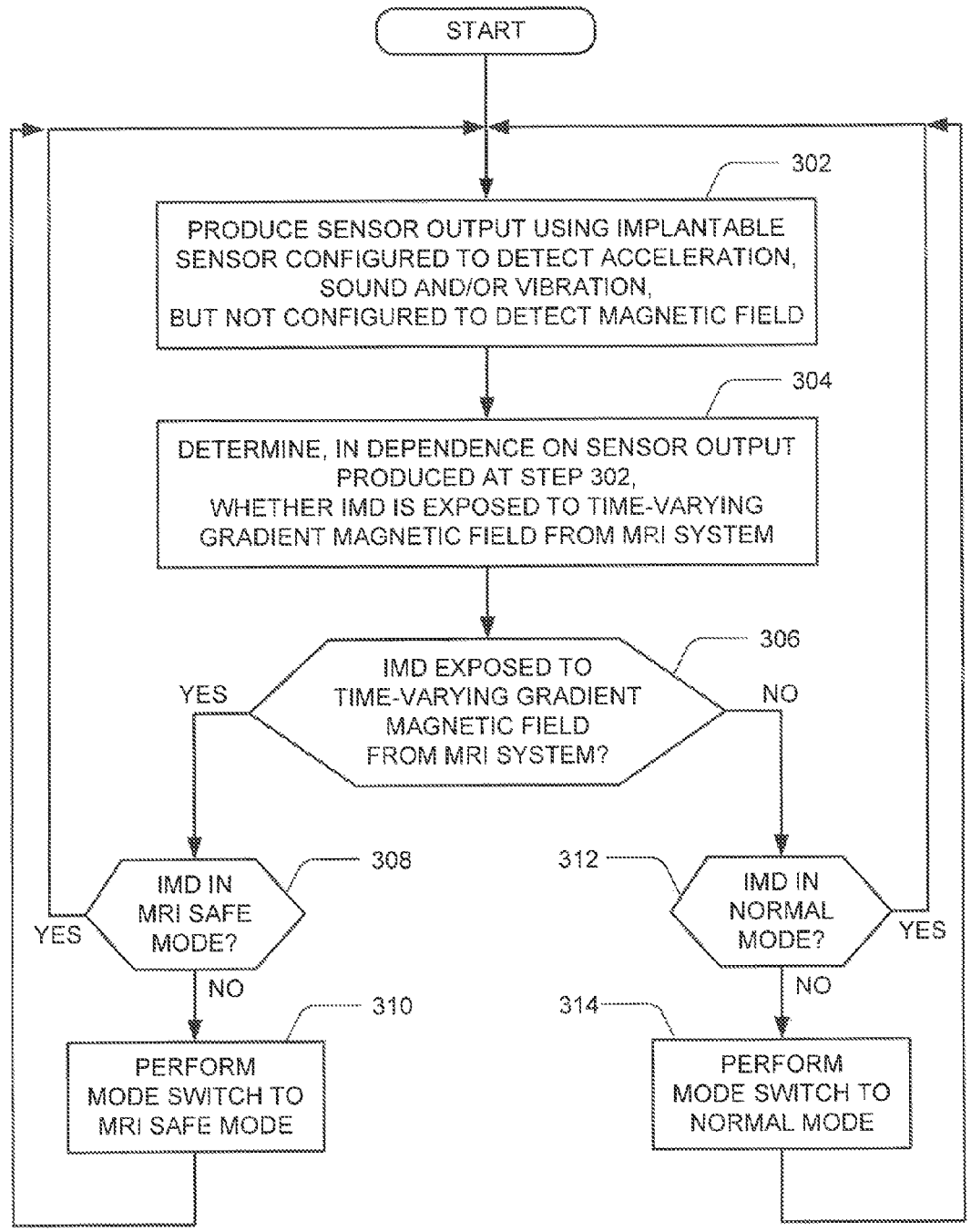
FIG. 3A is a high level flow diagram that is used to describe techniques to determine whether an IMD is being exposed to a magnetic field from an MRI system, according to specific embodiments of the present invention.

FIG. 3A is a high level flow diagram that is used to describe techniques, according to specific embodiments of the present invention, for determining whether an IMD is being exposed to a magnetic field from an MRI system, and for responding thereto. Referring to FIG. 3A, at step 302, a sensor output is produced using an implantable sensor that is configured to detect acceleration, sound and/or vibration, but is not configured to detect a magnetic field. Exemplary sensors that can be used to perform step 302 were discussed above with reference to the sensor 219 of FIG. 2. As was explained above in the discussion of the sensor 219 in FIG. 2, the sensor 219 used to perform step 302 can be an accelerometer, a strain gauge, or a microphone type sensor, but is not limited thereto. Where the sensor 219 is a 1-dimensional sensor, the sensor output is likely a single sensor output signal. By contrast, where the sensor 219 is a 2-dimensional or 3-dimensional sensor, then the sensor output is likely two or three sensor output signals.

At step 304, there is a determination, in dependence on the sensor output produced at 302, of whether the IMD is being exposed to a time-varying gradient magnetic field from an MRI system. Where the sensor output is a single sensor output signal, that single sensor output signal can be analyzed at step 304. Where the sensor output includes multiple (e.g., two or three) sensor output signals, each of the multiple signals can be analyzed individually, or a composite signal can be produced and analyzed, or the output signal having the greatest power can be identified and analyzed at step 304. Additional details of step 304 are discussed below.

At decision step 306, there is a decision as to whether or not step 304 resulted in a determination that the IMD is being exposed to a time-varying gradient magnetic field from an MRI system. If the answer to step 306 is yes, then at decision step 308 there is a decision as to whether or not the IMD is already in an MRI safe mode. If the answer to step 308 is no, because the IMD is in its normal operational mode, then there is a mode switch from the normal operational mode to the MRI safe mode, as indicated at step 310. If the answer to step 308 is yes, because the device is already in its MRI safe mode, then there is no need for a mode switch, and flow returns to step 302 (immediately, or after a specified delay, e.g., 30 seconds).

The normal operational mode can be the operational mode of the IMD prior to it being switched to the MRI safe mode. Thus, for cardiac rhythm management CORM") type IMDs, such as Brady and/or Tachy devices, for example, the normal operational mode is the CRM device's initially programmed mode. The term "MRI safe mode", as used herein, can refer to any operational mode of an IMD that is a safe operational mode in the presence of the magnetic fields generated by MRI systems. For example, for a Brady device (as well as a Brady engine in a Tachy device) an MRI safe mode might be a fixed-rate and/or non-demand (or asynchronous) pacing mode, as opposed to a rate-responsive and/or demand pacing mode. In some embodiments, an MRI safe mode can be both a non-demand mode (i.e., VOO) and a non-rate-responsive mode. Thus, in accordance with one embodiment, switching a Brady device to an MRI safe mode might entail mode switching to a VOO, AOO or DOO pacing mode.

The MRI safe mode to which the IMD is switched will typically depend on the normal operational mode of the IMD. In one embodiment, an IMD whose normal operational modes is a Dxx mode (e.g., a DDDR, DDD, DDI, or DVI mode) can perform a mode switch to OOO when exposed to a magnetic field generated by an MRI system (i.e., the MRI safe mode can be a DOO mode). In another embodiment, for an IMD whose normal operational mode is a Vxx mode (e.g., a VDDR, VDD, VDI, or DVI mode), the MRI safe mode can be a VOO mode. In still another embodiment, for an IMD having an Axx mode as its normal operational mode (e.g., an ADDR, ADD, ADI, or AVI mode), the MRI safe mode can be an AOO mode. These are just a few examples, which are not meant to be all encompassing.

In alternative embodiments, an MRI safe mode for a Tachy device might comprise turning-off tachy detection and/or therapy, as well as switching to a fixed-rate, non-demand pacing mode. In these embodiments, turning the tachy detection off will ensure that noise which might be induced on the device leads by an MRI scan is not mistaken by the device for a tachycardia, which might result in an inappropriate shock during an MRI. Also, for CRM devices, there may be other modes of operation that are considered safe in an MRI environment, so embodiments of the present invention are not limited to the MRI safe modes discussed herein. Further, as one of ordinary skilled in the art will appreciate, other types of IMDs will have different mode types that might be considered safe in an MRI environment, and those modes can be considered MRI safe modes.

Returning to step 306, if the answer to step 306 is no, then at decision step 312 there is a decision as to whether or not the IMD is already in its normal operational mode. If the answer to step 312 is no, then there is a mode switch to the normal operational mode at step 314. If the answer to step 312 is yes, because the device is already in its normal operational mode, then there is no need for a mode switch, and flow returns to step 302 (immediately, or after a specified delay, e.g., 30 seconds).

In certain embodiments, the steps in the flow diagram described with reference to FIG. 3A are not triggered until an implantable magnetic field detector sensor, such as a GMR sensor (e.g., the GMR sensor 217 in FIG. 2), detects a magnetic field. Alternatively, the steps in the flow diagram described with reference to FIG. 3A may not be triggered until a reed switch within the IMD is closed in response to a magnetic field. As explained above, a GMR sensor or a reed switch is often included within an IMD to detect when small handheld magnet is brought close to the IMD, e.g., to cause the device to switch into a "magnet mode", which can cause the recording an IEGM, performance of a battery check, change of the pacing rate to a value that corresponds to the battery voltage level or remaining longevity, and/or can cause tachycardia therapy to be suspended.

Figure 3B:
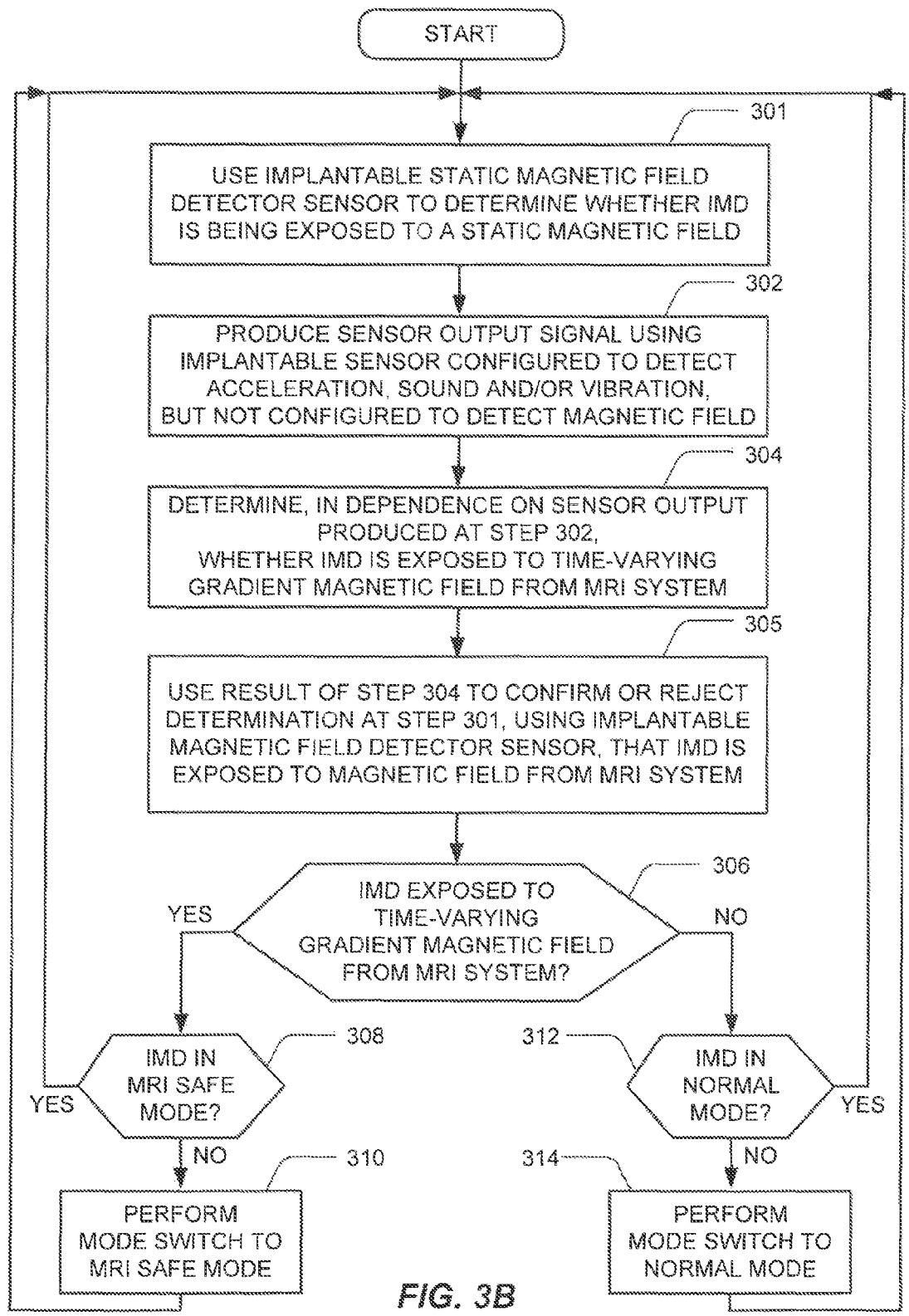
FIG. 3B is a high level flow diagram that is used to describe techniques to confirm whether an IMD is being exposed to a magnetic field from an MRI system, according to specific embodiments of the present invention.

Referring now to FIG. 3B, in certain embodiments, the implantable sensor that is configured to detect acceleration, sound and/or vibration, but is not configured to detect a magnetic field (such as the sensors discussed above with reference to the sensor 219 is FIG. 2), can be used to confirm or reject a determination, by an implantable MRI static magnetic field detector sensor (e.g., sensor 221 in FIG. 2), that the IMD is being exposed to a magnetic field from an MRI system.

Referring to FIG. 3B, at step 301 an implantable static magnetic field detector sensor is used to determine whether the IMD is being exposed to a static magnetic field, e.g., from an MRI system. Exemplary static magnetic field detector sensors were discussed above with reference to the sensor 221 in FIG. 2. For example, the static magnetic field detector sensor 221 can be a Hall effect sensor, but is not limited thereto. In the embodiments of FIG. 3B, the detection of a static magnetic field believed to be from an MRI system, by an implantable static magnetic field detector sensor (e.g., 221 in FIG. 2), triggers the performance of steps 302 and 304. Since steps 302 and 304 were already described above with reference to FIG. 3A, they need not be described again.

At step 305, the result of step 304 is used to confirm or reject the determination at step 301 (using an implantable static magnetic field detector sensor, e.g., 221) that the IMD is being exposed to a magnetic field from an MRI system. If there is confirmation at step 305 that the IMD is being exposed to a magnetic field from an MRI system, then the answer to decision step 306 will be yes. If there is not a confirmation at step 305 that the IMD is being exposed to a time-varying gradient magnetic field from an MRI system (i.e., if there is a rejection at step 305), then the answer to decision step 306 will be no. The flow thereafter proceeds in the same manner discussed above with regard to FIG. 3A. Since steps 306, 308, 310, 312 and 314 were already described above with reference to FIG. 3A, they need not be described again. In an alternative embodiment, at step 301 there is simply a determination of whether the IMD is being disposed to a static magnetic field (whether it be from a handheld magnet or an MRI system); and at step 305 there is a determination, based on the results of step 304, of whether the static magnetic field detected at step 301 is from a handheld magnet or from an MRI system. In other words, the results of step 304 can be used to discriminate between exposure to a magnetic field produced by a handheld magnet and a magnetic field produced by an MRI system.

Figure 4:
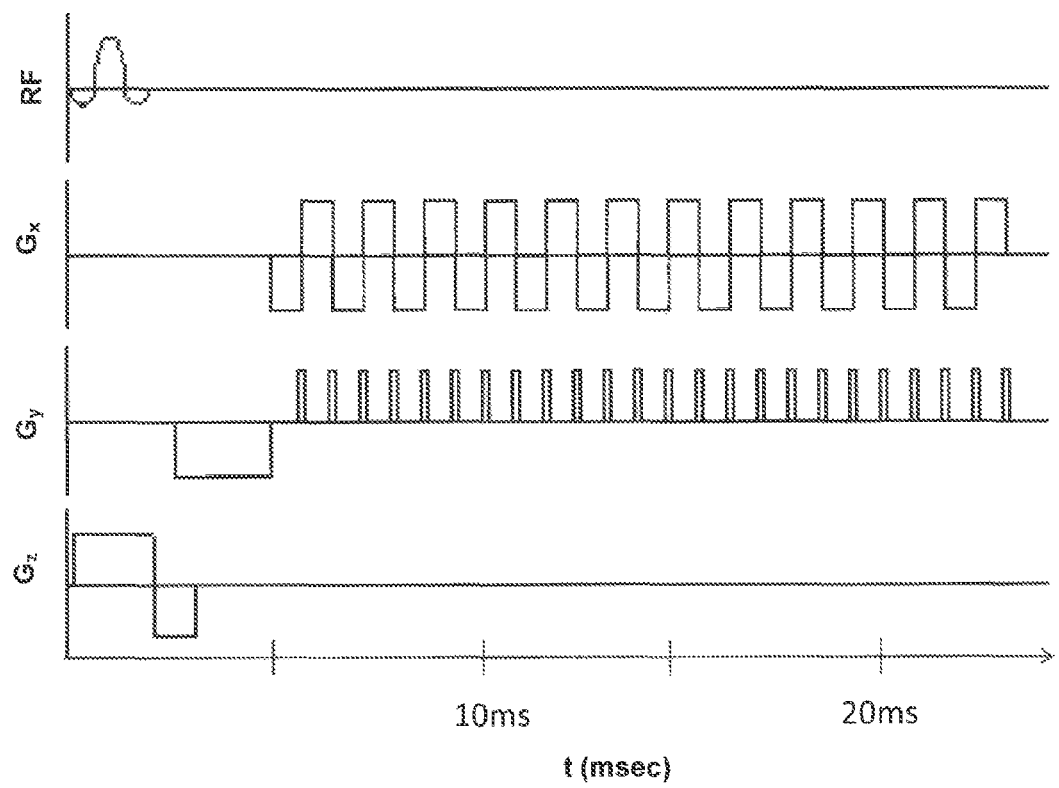
FIG. 4 illustrates exemplary components of a time-varying magnetic field sequence produced by an MRI system.

Reference is now made to FIG. 4, which illustrates exemplary components of a time-varying magnetic field sequence generated by an exemplary MRI system. The time-varying magnetic field sequence represented in FIG. 4 includes an RF component (shown in the uppermost plot), and time-varying gradient components (shown in the bottom three plots). When the sensor 219 is exposed to the time-varying magnetic field represented in FIG. 4, the one or more output signals produced by the sensor 219 may resemble a combination of the Gx, Gy and Gz waveforms of FIG. 4 (i.e., a combination of the bottom three plots). The one or more output signals produced by the sensor 219 can be analyzed in the time domain and/or the frequency domain at step 304 (in FIGS. 3A and 3B), to determine whether the IMD is being exposed to a time-varying gradient magnetic field from an MRI system. Various different techniques can be used to perform step 304, some of which are discussed below.

In accordance with an embodiment, at step 304 the output signal(s) produced by the sensor 219 can be analyzed in the time domain by counting the number of zero crossing, peaks and/or other features of the signal(s) that occur within a time-window, and comparing the resulting count(s) to a corresponding threshold(s). In accordance with another embodiment, the morphology of the output signal(s) produced by the sensor 219 can be compared to one or more stored templates of time-varying gradient magnetic field sequences produced by MRI systems, and the results of the comparison(s) can be compared to a corresponding threshold. For example, because a single MRI system typically utilizes multiple (i.e., a set of) time-varying gradient magnetic field sequences, and different MRI systems utilize different sets of time-varying gradient magnetic field sequences, a template can be stored for each known or likely sequence, or one or more composite sequence templates can be stored. In each of the above embodiments, if a corresponding threshold is exceeded, then there is a determination that the IMD is being exposed to a time-varying gradient magnetic field. Such thresholds can be determined, e.g., through experimentation with various different commercially available MRI systems and/or simulations thereof. Such templates and/or thresholds can be reprogrammed or otherwise update (e.g., using telemetry) to account for new MRI systems that become available.

One of ordinary skill in the art will appreciate, from the description herein, that there are various ways in which the output signal(s) produced by the sensor 219 can be analyzed in the time domain to determine, at step 304, whether the IMD is being exposed to a time-varying gradient magnetic field from an MRI system. For example, portions of the signal(s) can be integrated over time, and the results of the integration can be compared to a threshold. It would also be possible to analyze morphological signals widths and/or slopes of the output signal(s) produced by the sensor 219. These are just a few examples, which are not meant to be all encompassing.

Alternatively, or additionally, at step 304 the frequency content of the output signal(s) produced by the sensor 219 can be determined or estimated, and the determination of whether the IMD is being exposed to a time-varying gradient magnetic field from an MRI system can be based on the estimated or otherwise determined frequency content of the sensor output.

Figure 5A:
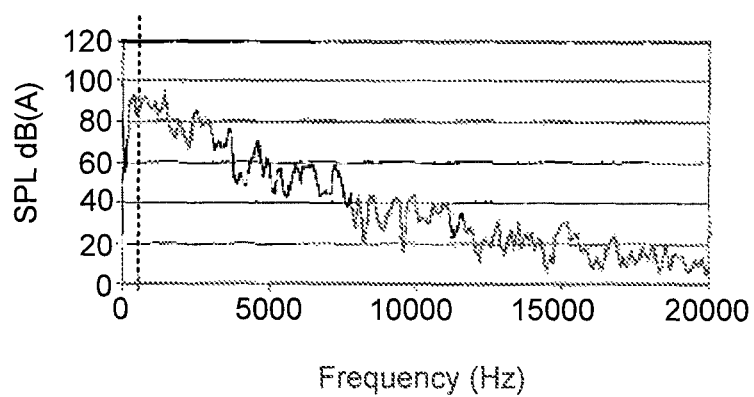
FIGS. 5A, 5B and 5C illustrate exemplary plots of the frequency content associated with three different time-varying gradient magnetic field sequences.
Figure 5B:
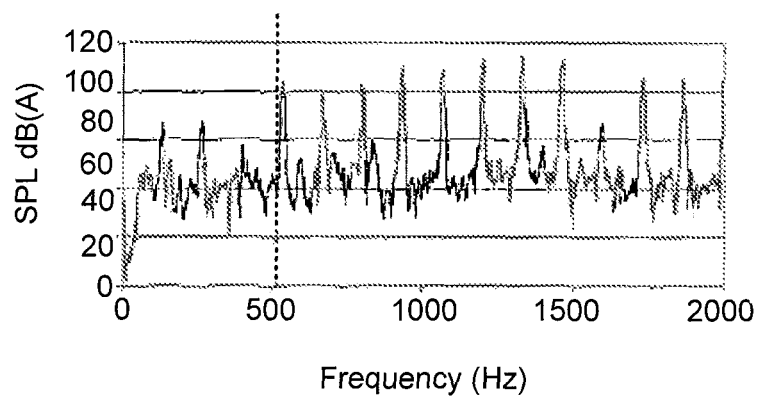
Figure 5C:
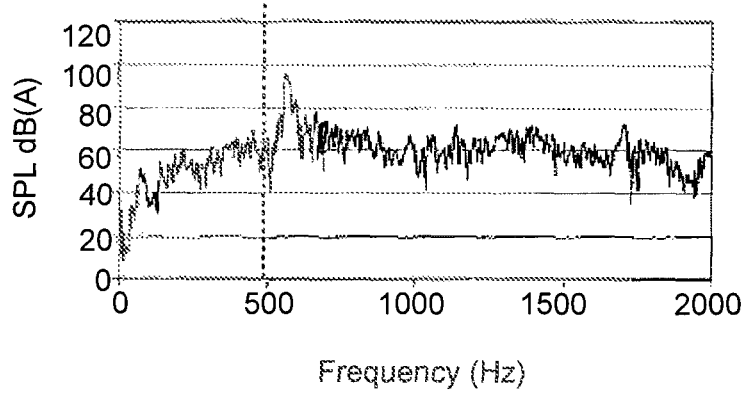

FIGS. 5A, 5B and 5C illustrate exemplary plots of the frequency content associated with three different time-varying gradient magnetic field sequences. Notice that at about 500 Hz in each plot (which is identified by a vertical dashed line in each plot), there is a relatively large amount of power present. For example, in FIG. 5A, at 500 Hz the sound pressure level (SPL) exceeds 80 dB(A); in FIG. 5B, at 500 Hz the SPL exceeds 40 dB(A); and in FIG. 5C, at 500 Hz the SPL exceeds 50 dB(A). Accordingly, if a threshold were set at about 35 dB(A), then regardless of which one of the time-varying gradient magnetic field sequences was being used, there would be a determination at step 304 that the IMD is being exposed to a time-varying gradient magnetic field from an MRI system.

There are various ways in which the frequency content of the output signal(s), produced by the sensor 219, can be used to determine whether an IMD is being exposed to a time-varying gradient magnetic field from an MRI system at step 304, some of which are described below.

In accordance with an embodiment, a fast Fourier transform (FFT) is performed on one or more sensor output signals, or a composite of multiple sensor output signals, produced by the sensor 219. The results of the FFT can then be used to determine whether the IMD is being exposed to a time-varying gradient magnetic field from an MRI system. In some embodiments, the morphology of the results of an FFT can be compared to corresponding frequency content templates of time-varying gradient magnetic field sequences produced by MRI systems, and the results of the comparison(s) can be compared to a corresponding threshold, to determine whether the IMD is being exposed to time-varying gradient magnetic field produced by an MRI system. Alternatively, or additionally, the magnitude of the results of an FFT can be compared to a corresponding threshold, to determine whether the IMD is being exposed to a time-varying gradient magnetic field from an MRI system.

Instead of (or in addition to) performing an FFT, a wavelet transformation can be performed on one or more sensor output signals, or a composite of multiple sensor output signals, produced by the sensor 219. In some embodiments, the morphology of the results of a wavelet transformation can be compared to corresponding frequency content versus time templates of time-varying gradient magnetic field sequences produced by MRI systems, and the results of the comparison(s) can be compared to a corresponding threshold, to determine whether the IMD is being exposed to time-varying gradient magnetic field produced by an MRI system. Alternatively, or additionally, the magnitude of the results of a wavelet transformation can be compared to a corresponding threshold, to determine whether the IMD is being exposed to a time-varying gradient magnetic field from an MRI system. Other ways to analyze the frequency content of the output signal(s), produced by the sensor 219, include determining the power spectral density (PSD) of the signal(s), and comparing the determined PSD to one or more corresponding template(s) and/or threshold(s).

Preferably, for each of the above described embodiments, the templates and/or thresholds should be selected so as to minimize the probability that vibrations and/or acoustic noise from other sources (i.e., sources other than MRI systems) cause IMDs to falsely determine that they are being exposed to time-varying gradient magnetic field sequences produced by MRI systems.

Embodiments of the present invention have been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. 3A and 3B. For another example, it is possible to change the boundaries of some of the blocks shown in FIG. 2.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. A method for use with an implantable medical device (IMD), comprising:
   (a) using an implantable magnetic field detector sensor to detect a magnetic field; and (b) in response to detecting a magnetic field using the implantable magnetic field detector sensor, determining, in dependence on a sensor output produced using an implantable sensor that is configured to detect acceleration, sound and/or vibration, whether the IMD is being exposed to a time-varying gradient magnetic field from a magnetic resonance imaging (MRI) system;

wherein the implantable sensor that is configured to detect acceleration, sound and/or vibration is not configured to detect a magnetic field.

2. The method of claim 1, further comprising:
(c) performing a mode switch to an MRI safe mode if, at step (b), there is a determination that the IMD is being exposed to a time-varying magnetic field from an MRI system.

3. The method of claim 2, further comprising:
(d) after a mode switch is performed to switch the IMD from the normal operational mode to the MRI safe mode, determining, using at least one of the implantable magnetic field detector and the sensor that is configured to detect acceleration, sound and/or vibration, when to switch the IMD back to the normal operational mode.

4. The method of claim 1, wherein step (a) comprises using an implantable giant magnetoresistance (GMR) sensor, reed switch or Hall effect sensor to detect a magnetic field.

5. The method of claim 1, wherein:
step (a) is performed to determine whether the IMD is being exposed to a magnetic field from an MRI system; and
step (b) is performed in response a determination, using the implantable magnetic field detector sensor, that the IMD is being exposed to a magnetic field from an MRI system; and
using results of step (b) to confirm or reject the determination at step (a), using the implantable magnetic field detector sensor, that the IMD is being exposed to a magnetic field from an MRI system.

6. The method of claim 1, wherein step (b) includes:
(b.1) producing one or more accelerometer output signals using an implantable accelerometer that is configured to detect acceleration, sound and/or vibration, but is not configured to detect a magnetic field; and
(b.2) determining, in dependence on the accelerometer output signal(s), whether the IMD is being exposed to a time-varying gradient magnetic field from an MRI system.

7. The method of claim 1, wherein step (b) comprises comparing a morphology of one or more signals output by the implantable sensor to one or more templates corresponding to one or more representative sets of time-varying gradient magnetic field sequences produced by MRI systems.

8. A method for use with an implantable medical device (IMD), comprising:
(a) producing a sensor output using an implantable sensor that is configured to detect acceleration, sound and/or vibration, but is not configured to detect a magnetic field; and
(b) determining, in dependence on the sensor output produced at step (a), whether the IMD is being exposed to a time-varying gradient magnetic field from a magnetic resonance imaging (MRI) system;
wherein step (b) comprises
(b.1) estimating or otherwise determining frequency content of the sensor output by performing a fast Fourier transform (FFT), performing a wavelet transformation and/or determining a power spectral density (PSD) of the sensor output; and
(b.2) determining, based on the estimated or otherwise determined frequency content of the sensor output, whether the IMD is being exposed to a time-varying gradient magnetic field from an MRI system.

9. The method of claim 8, wherein step (b.2) comprises:
(b.2.i) comparing the estimated or otherwise determined frequency content of the sensor output to frequency content corresponding to one or more representative sets of time-varying gradient magnetic field sequences produced by MRI systems; and
(b.2.ii) determining, based on results of the comparing at step (b.2.i), whether the IMD is being exposed to a time-varying gradient magnetic field from an MRI system.

10. A method for use with an implantable medical device (IMD), comprising:
(a) producing a sensor output using an implantable sensor that is configured to detect acceleration, sound and/or vibration, but is not configured to detect a magnetic field; and
(b) determining, in dependence on the sensor output produced at step (a), whether the IMD is being exposed to a time-varying gradient magnetic field from a magnetic resonance imaging (MRI) system;
wherein step (b) comprises
(b.1) counting a number of zero crossings, peaks or other signal features within a window of one or more signals output by the implantable sensor; and
(b.2) determining, based on results of the counting at step (b.1), whether the IMD is being exposed to a time-varying gradient magnetic field from an MRI system.

11. An implantable medical device (IMD), comprising:
an implantable magnetic field detector sensor configured to detect a magnetic field;
an implantable sensor configured to
detect acceleration, sound and/or vibration, and
produce an output indicative of detected acceleration, sound and/or vibration; and
an MRI detector configured to determine, in dependence on the sensor output indicative of detected acceleration, sound and/or vibration, whether the IMD is being exposed to a time-varying gradient magnetic field from a magnetic resonance imaging (MRI) system;
wherein the implantable sensor, which is configured to detect acceleration, sound and/or vibration, is not configured to detect a magnetic field; and
wherein a determination by the MRI detector, in dependence on the sensor output indicative of detected acceleration, sound and/or vibration, is triggered in response to the magnetic field detector sensor detecting a magnetic field.

12. The IMD of claim 11, further comprising:
a controller configured to perform a mode switch to an MRI safe mode in response to a determination by the MRI detector, in dependence on the sensor output, that the IMD is being exposed to a time-varying gradient magnetic field from an MRI system.

13. The IMD of claim 11, wherein the implantable magnetic field detector sensor comprises an implantable giant magnetoresistance (GMR) sensor, reed switch or Hall effect sensor.

14. The IMD of claim 11,
wherein the MRI detector is configured to use the output indicative of detected acceleration, sound and/or vibration, produced by the implantable sensor configured to detect acceleration, sound and/or vibration, to confirm or reject a detection, by the implantable magnetic field detector sensor, that the IMD is being exposed to a magnetic field from an MRI system.

15. The IMD of claim 11, wherein the MRI detector is configured to:
estimate or otherwise determine frequency content of the sensor output; and
determine, based on the estimated or otherwise determined frequency content of the sensor output, whether the IMD is being exposed to a time-varying gradient magnetic field from an MRI system.

16. The IMD of claim 11, wherein:
the implantable sensor, which is configured to detect acceleration, sound and/or vibration, and is not configured to detect a magnetic field, comprises an accelerometer sensor; and
the MRI detector is configured to determine, in dependence on one or more output signals output by the accelerometer sensor, whether the IMD is being exposed to a time-varying gradient magnetic field from an MRI system.

17. The IMD of claim 11, wherein the implantable sensor, which is configured to detect acceleration, sound and/or vibration, and is not configured to detect a magnetic field, is selected from the group consisting of:
an accelerometer sensor;
a strain gauge sensor; and
a microphone sensor.

18. An implantable medical device (IMD), comprising:
an implantable magnetic field detector sensor configured to determine whether the IMD is being exposed to a magnetic field;
an implantable accelerometer sensor;
an MRI detector configured to determine, in dependence on the one or more signals output by the implantable accelerometer sensor, whether the IMD is being exposed to a time-varying gradient magnetic field from a magnetic resonance imaging (MRI) system; and
a controller configured to perform a mode switch to an MRI safe mode in response to a determination by the MRI detector, in dependence on the one or more signals output by the implantable accelerometer sensor, that the IMD is being exposed to a time-varying gradient magnetic field from an MRI system;
wherein a determination by the MRI detector, in dependence on the signal(s) output by the implantable accelerometer sensor, is triggered in response to the magnetic field detector sensor detecting a magnetic field.

19. The IMD of claim 18, further comprising:
one or more pulse generators configured to produce pacing pulses, cardioverting pulses, and/or defibrillator pulses; and
sensing circuitry configured to sense cardiac electrical activity;
wherein the controller is configured to disable the sensing circuitry or ignore electrogram signals produced by the sensing circuitry, when the IMD is in the MRI safe mode.

20. The IMD of claim 18, wherein the implantable magnetic field detector sensor comprises an implantable giant magnetoresistance (GMR) sensor, reed switch or Hall effect sensor configured to detect a magnetic field.

21. The IMD of claim 18, wherein:
the implantable magnetic field detector sensor comprises a static magnetic field detector sensor configured to determine whether the IMD is being exposed to a static magnetic field; and
a determination by the MRI detector, in dependence on the one or more signals output by the implantable accelerometer sensor, is used to confirm or reject a determination, using the static magnetic field detector sensor, that the IMD is being exposed to a magnetic field from an MRI system.

22. The IMD of claim 18, wherein:
the implantable magnetic field detector sensor comprises a static magnetic field detector sensor configured to determine whether the IMD is being exposed to a static magnetic field;
wherein a determination by the MRI detector, in dependence on the one or more signals output by the implantable accelerometer sensor, is triggered in response to the static magnetic field detector sensor detecting a static magnetic field; and
wherein a determination by the MRI detector, in dependence on the one or more signals output by the implantable accelerometer sensor, is used to distinguish between
(a) the IMD being exposed to a magnetic field from a handheld magnet, and
(b) the IMD is being exposed to a magnetic field from an MRI system.

23. A method for use with an implantable medical device (IMD), comprising:
(a) using an implantable magnetic field detector sensor to detect a magnetic field;
(b) using an implantable sensor to detect secondary acoustic and/or vibratory effects of a magnetic resonance imaging (MRI) system, wherein the implantable sensor is not configured to detect a magnetic field; and
(c) using results of both steps (a) and (b) to determine whether to switch the IMD from a normal operational mode to an MRI safe mode.

24. A method for use with an implantable medical device (IMD), comprising:
(a) using an implantable microphone sensor to detect secondary acoustic effects of a magnetic resonance imaging (MRI) system; and
(b) determining, in dependence on the secondary acoustic effects detected by the implantable microphone sensor, whether to switch the IMD from a normal operational mode to an MRI safe mode.

* * * * *